US008865790B2

(12) United States Patent  (10) Patent No.: US 8,865,790 B2
Koltisko et al.  (45) Date of Patent: Oct. 21, 2014

(54) DENTAL MATERIALS USING 2,2,4,4-TETRAMETHYL-1,3-CYCLOBUTANEDIOL

(75) Inventors: Bernard Koltisko, Milton, DE (US); Xiaoming Jin, Middletown, DE (US)

(73) Assignee: DENTSPLY International Inc., York, PA (US)

( * ) Notice: Subject to any disclaimer, the term of this patent is extended or adjusted under 35 U.S.C. 154(b) by 0 days.

(21) Appl. No.: 12/949,883

(22) Filed: Nov. 19, 2010

(65) Prior Publication Data

US 2011/0144230 A1  Jun. 16, 2011

Related U.S. Application Data

(60) Provisional application No. 61/281,713, filed on Nov. 20, 2009.

(51) Int. Cl.
- *A61K 6/083* (2006.01)
- *A61K 6/09* (2006.01)
- *C08G 18/04* (2006.01)
- *A61C 5/00* (2006.01)
- *C08L 75/04* (2006.01)

(52) U.S. Cl.
CPC .. *A61K 6/083* (2013.01); *A61K 6/09* (2013.01)
USPC ........... 523/116; 523/117; 528/65; 433/228.1

(58) Field of Classification Search
USPC ................... 523/116, 117; 528/65; 433/228.1
See application file for complete search history.

(56) References Cited

U.S. PATENT DOCUMENTS

| | | | |
|---|---|---|---|
| 2,936,324 A | 5/1960 | Hasek et al. | |
| 3,038,884 A * | 6/1962 | Martin et al. | 528/85 |
| 3,375,210 A | 3/1968 | D'Onofrio | |
| 3,527,734 A | 9/1970 | Matzner | |
| RE29,772 E * | 9/1978 | Niederhauser et al. | 525/440.072 |
| 4,255,243 A * | 3/1981 | Coqueugniot et al. | 522/14 |
| 5,169,994 A | 12/1992 | Summer, Jr. et al. | |
| 5,258,556 A | 11/1993 | Summer, Jr. et al. | |
| 6,184,286 B1 * | 2/2001 | Edwards et al. | 524/507 |
| 6,255,437 B1 | 7/2001 | Walker et al. | |
| 6,444,721 B2 * | 9/2002 | Schwalm et al. | 522/84 |
| 7,098,274 B2 * | 8/2006 | Wu et al. | 525/467 |
| 7,476,707 B2 * | 1/2009 | Wu et al. | 524/847 |
| 7,521,583 B2 | 4/2009 | McCusker-Orth et al. | |
| 7,524,994 B2 | 4/2009 | McCusker-Orth et al. | |
| 7,560,600 B2 | 7/2009 | McCusker-Orth et al. | |
| 7,576,171 B2 | 8/2009 | Crawford et al. | |

FOREIGN PATENT DOCUMENTS

| | | |
|---|---|---|
| GB | 965762 | 8/1964 |
| GB | 1156222 | 6/1969 |

* cited by examiner

*Primary Examiner* — Tae H Yoon
(74) *Attorney, Agent, or Firm* — Leana Levin; Douglas J. Hura; David A. Zdurne

(57) ABSTRACT

Dental compositions and dental products having a resin derived from a cyclic diol such as 2,2,4,4-tetramethyl-1,3-cyclobutanediol.

17 Claims, 7 Drawing Sheets

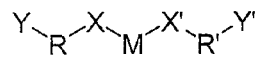 (1)

General Structure of TMCD-based Resins

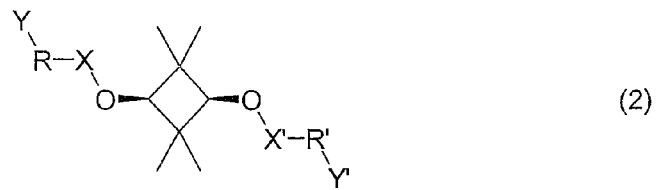 (2)

Resin Structure based on *cis*-TMCD

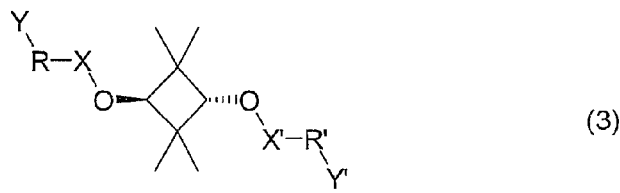 (3)

Resin Structure based on *trans*-TMCD

M: TMCD moiety(cis- and/or trans-isomer)
X or X': same or different carbonate, ester, urethane, ether linkage
R or R': same or different alkyl, alicyclic, aromatic residues or substitutes aromatic residues etc;
Y or Y': same or different polymerizable groups such as vinyl, vinylether, acrylic, methacrylic, epoxide, etc

FIGURE 1A

DENTAL MATERIALS USING 2,2,4,4-TETRAMETHYL-1,3-CYCLOBUTANEDIOL

The present application is non-provisional application claiming priority from U.S. Provisional Application No. 61/281,713, filed on Nov. 20, 2009.

TECHNICAL FIELD

Disclosed herein are dental materials and dental products comprising a cyclic diol such as 2,2,4,4-tetramethyl-1,3-cyclobutanediol (TMCD).

BACKGROUND

Dental materials such as for example, dental filling materials, often include liquid polymerizable organic monomers and/or polymers, reactive diluents, polymerization initiators, stabilizers, and fillers. Such composite materials have their good mechanical properties such as high flexural strengths, high compressive strengths and hardness. Further, they are often polishable and readily accept suitable dyes. The most frequently used monomers are esters of methacrylates and higher multifunctional alcohols or isocyanates such as the bismethacrylate of biphenol-A diglycidyl ether, urethane bismethacrylates. Aromatic diols are often used to make polymerizable resins having good thermal and mechanical stability.

Bisphenol A (2,2-bis(4-hydroxyphenyl)propane, BPA) in particular is one such aromatic diol that has been widely used in epoxy resin, modified methacrylate resin, polyethersulfone/ketone, polyester, polycarbonate and the like, for use in dental materials. Resins or polymers from fully aliphatic diols are less popular due to their relative lower thermal stability. However, there have been investigations of resins and polymers based on cyclic aliphatic compounds, especially those that are multi-cyclic. Interest in such cyclic aliphatic diols has increased due to potential concerns of some aromatic diol, especially BPA. Accordingly, BPA-free resins or polymers would be highly desirable if they possessed the same or comparable thermal and mechanical stabilities as the BPA counterparts.

SUMMARY

It has been unexpectedly found that 2,2,4,4-tetramethyl-1,3-cyclobutanediol (TMCD), which is a cyclic diol that is rigid, thermally stable, and which forms symmetric aliphatic molecules, is particularly useful in dental products such as restoratives and the like. According to the present disclosure, it is expected that such a moiety would provide improved optical, thermal and mechanical properties in comparison to linear aliphatic analogies. This diol is produced as a mixture of cis and trans isomers, depending on the relative stereochemistry of the hydroxyl groups. A standard reaction path for the synthesis of TMCD is as follows:

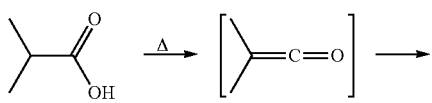

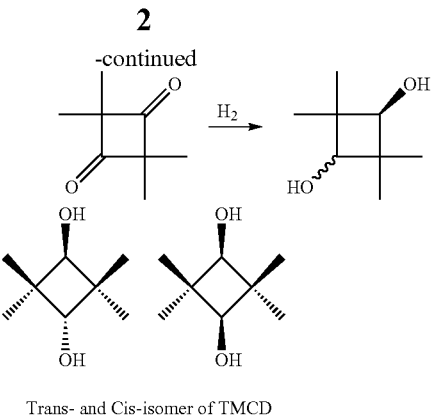

Trans- and Cis-isomer of TMCD

TMCD has been used in many polyesters or polycarbonates and is known to be a co-monomer. Some of key features from such polymers are its high impact resistance, optical clarity, thermal stability and biodegradability in addition to being BPA-free. Although TMCD as a diol comonomer has been taught in making some polymerizable/curable resins, TMCD is not known as a BPA alternative in dental applications.

BRIEF DESCRIPTION OF DRAWINGS

FIG. 1A shows the general structure of TMCD-based resins, including resin structures based on cis-TMCD and trans-TMCD.

DETAILED DESCRIPTION

Figure 1B:
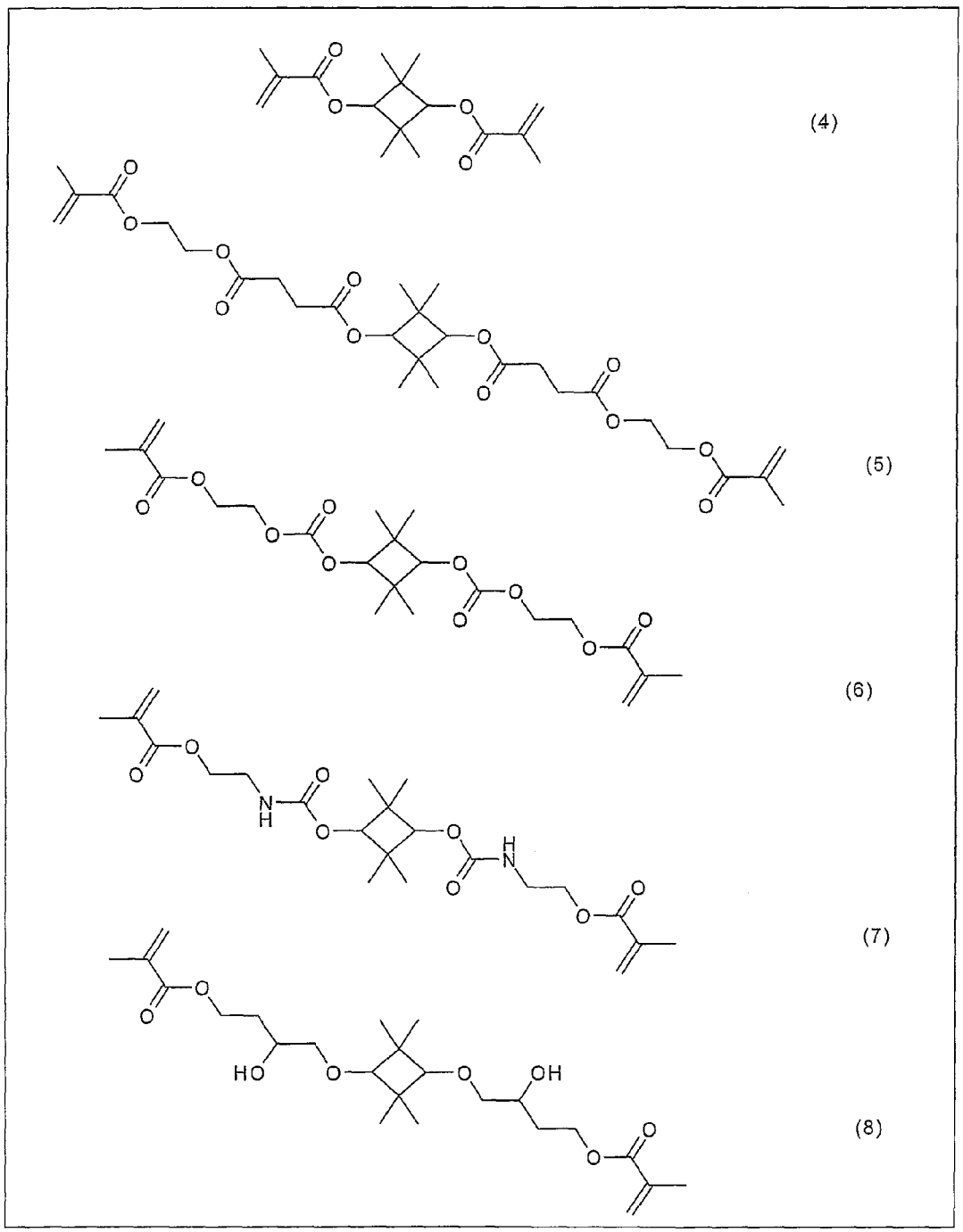
FIG. 1B shows the specific structure of various TMCD-based resins.

As stated above dental restorative materials, such as composites, adhesives, and cements have traditionally contained derivatives of BPA as the base polymeric component. These include monomers such as 2,2-bis[4-(2-hydroxy-3-methacryloyloxy-propoxy)phenyl]propane (Bis-GMA), 2,2-bis(4-methacryloyloxy-phenyl)propane (Bis-DMA), 2,2-bis[4-(2-methacryloyloxy-ethoxy)phenyl]propane (EBPADMA) and 2,2-bis[4-glycidyl-phenyl]propane (BADGE). There are also many examples of urethane resins produced by combining BPA and BPA derivatives with di-isocyanates. These components have provided exceptional properties such as high durability, chemical resistance and optical properties to formulated dental products.

Due to potential health concerns related human exposure to BPA, many producers of polymers which contain BPA and derivatives of BPA have been seeking new chemical approaches. For instance, TMCD has been shown to be an effective substitute for BPA in polyester resin systems.

As described herein, TMCD may be used as a building block for the development of new dental resin systems. Substantially the same synthetic approaches currently used to synthesize BPA derivatives may be employed when substituting TMCD for BPA based resins. TMCD is substituted for BPA in these reactions. The resultant TMCD derivatives are substituted for their BPA derivative analogues in restorative formulations. The result is that high performance dental restorative materials are made free of BPA containing materials.

It is therefore, an accomplishment of the present disclosure to provide the use of TMCD based monomers used in dental formulations and materials, including restorative composites, bonding agents, cements, luting agents, bases, and liners.

TMCD monomers with one or more pendant vinyl groups, such as, but not limited to methacrylic or acrylic moieties are also provided according to the invention. These compounds may also include groups such as ethylene oxide or propylene oxide in their composition.

The TMCD monomers used in the present invention may have one or more pendant epoxy groups. Urethane derivatives may also be provided, normally produced through reaction of TMCD with isocyanate based compounds. TMCD derivatives with phosphate, and other ionic functionalities, and TMCD derivatives which may contain combinations of functionalities are provided. Resins or macromonomers which may incorporate TMCD in its structure and dental formulations with TMCD based compounds are within the scope of the present disclosure.

Therefore, according to the present disclosure, a dental material is provided based upon a TMCD polymerizable resin. An example of such a dental product is a dental restorative that is light curable. Such a dental product or material may be placed into a prepared dental cavity and then exposed to electromagnetic radiation of an appropriate wavelength to initiate (or co-initiate if other initiators are useful) to polymerize the material. Before polymerization, the material must have suitable flow properties to allow it to be placed into the prepared cavity, yet may also be required to have a certain stiffness or resistance to flow to allow the dental practitioner the ability to manipulate it. Further, after polymerization, wear, toughness, fracture resistance, and other thermal and mechanical stabilities must be of a certain, desirable nature. While such aspects of dental restoratives are well developed with respect to BPA dental materials, it is unexpected that such properties are accomplished by TMCD materials. In fact, other BPA free materials do not exhibit the desirable properties that are exhibited by dental materials having TMCD resins, as described herein.

TMCD may be prepared in high yields by pyrolysis of isobutyric acid, or isobutyric anhydride to form dimethylketene, which spontaneously dimerizes to cyclic diketone. Hydrogenation of such diketone using ruthenium, nickel or rhodium catalysts produced up to 98% yield of cis/trans TMCD. The isolation of the pure isomers is tedious and expensive, so cis/trans mixtures of TMCD have been used.

Figure 2:
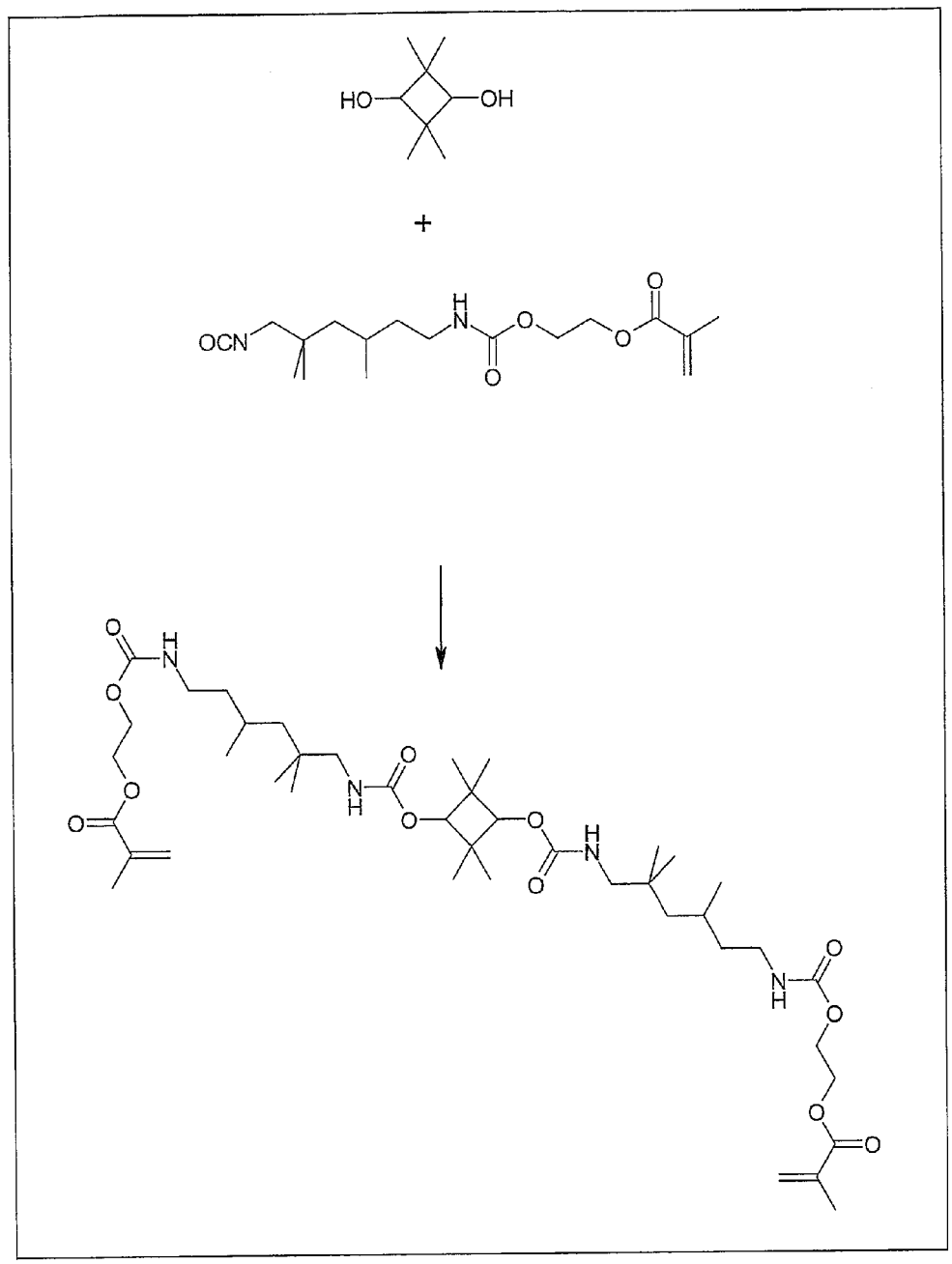
FIG. 2 shows a one-step reaction pathway of creating a urethane dimethacrylate oligomer of a TMCD-based resin.

Again TMCD is a diol molecule and it should be readily reacted with other condensation monomers to build up linkages such as ester, carbonate, urethane and the like (see FIG. 1) and to form polymerizable resins accordingly. Additional examples of TMCD-based polymerizable resins are given in FIG. 2. For example, if TMCD reacts with an isocyanate, it would yield a urethane-based resin; if TMCD reacts with a carboxylic monomer, and it would yield ester type of resin. The physical and mechanical properties of the resulting TMCD-based resins would vary depending upon the resin's linkages, detailed molecular structures and the pathways to make such resins.

Figure 3:
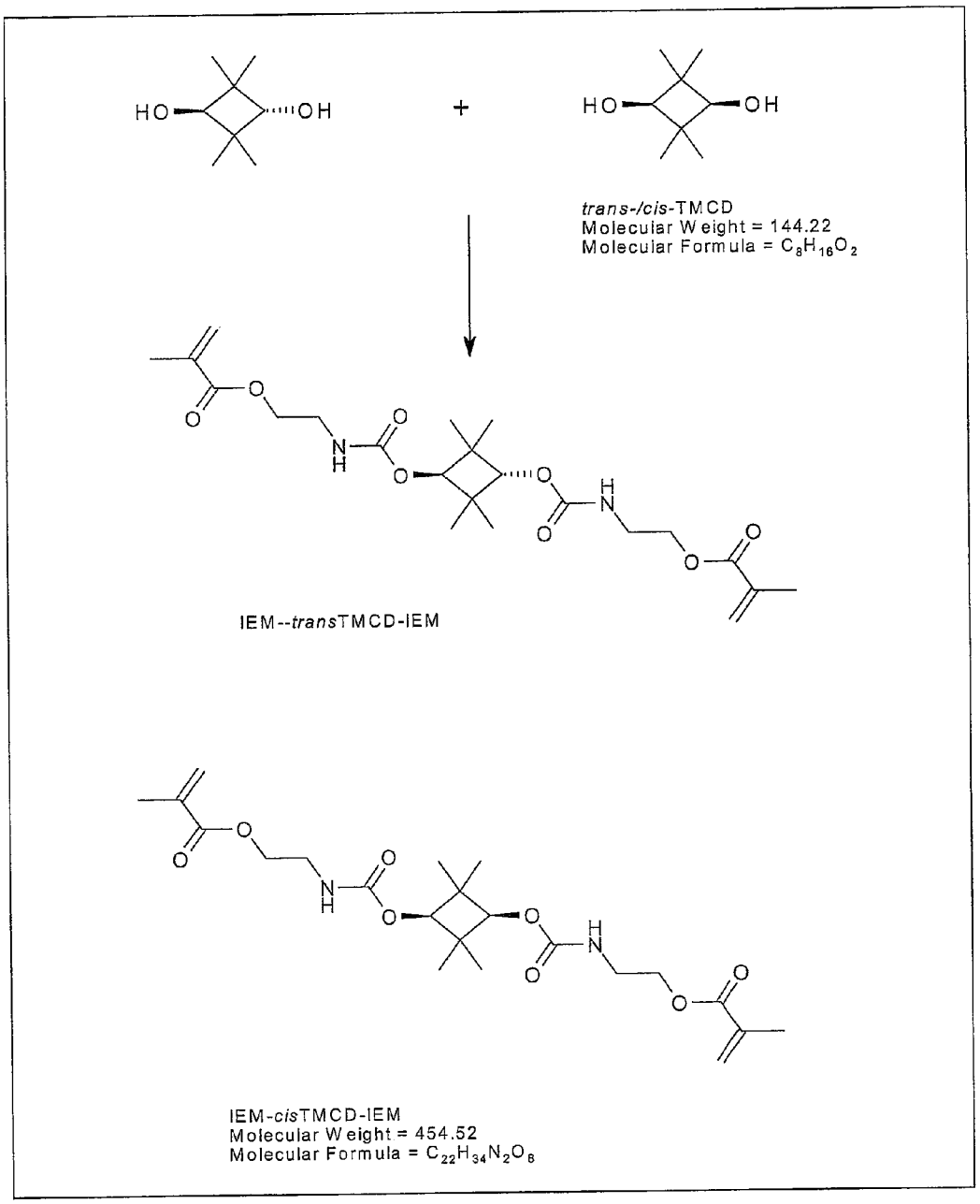
FIG. 3 shows a reaction pathway of creating a urethane dimethacrylate trimer of a TMCD-based resin.

In Table I, it is given some examples for TMCD-based polymerizable resins. In FIG. 3, there is shown a reaction pathway towards urethane type of polymerizable resin based on TMCD. This resulting urethane oligomeric resin is liquid. It can be further formulated with any other resin and conventional initiators to make it polymerizable. Thus, clear, rigid cured resin can be resulted after it is formulated with Camphorquinone (CQ) and ethyl-4-(dimethylamino)benzoate (EDAB) and exposed to visible light.

Figure 4:
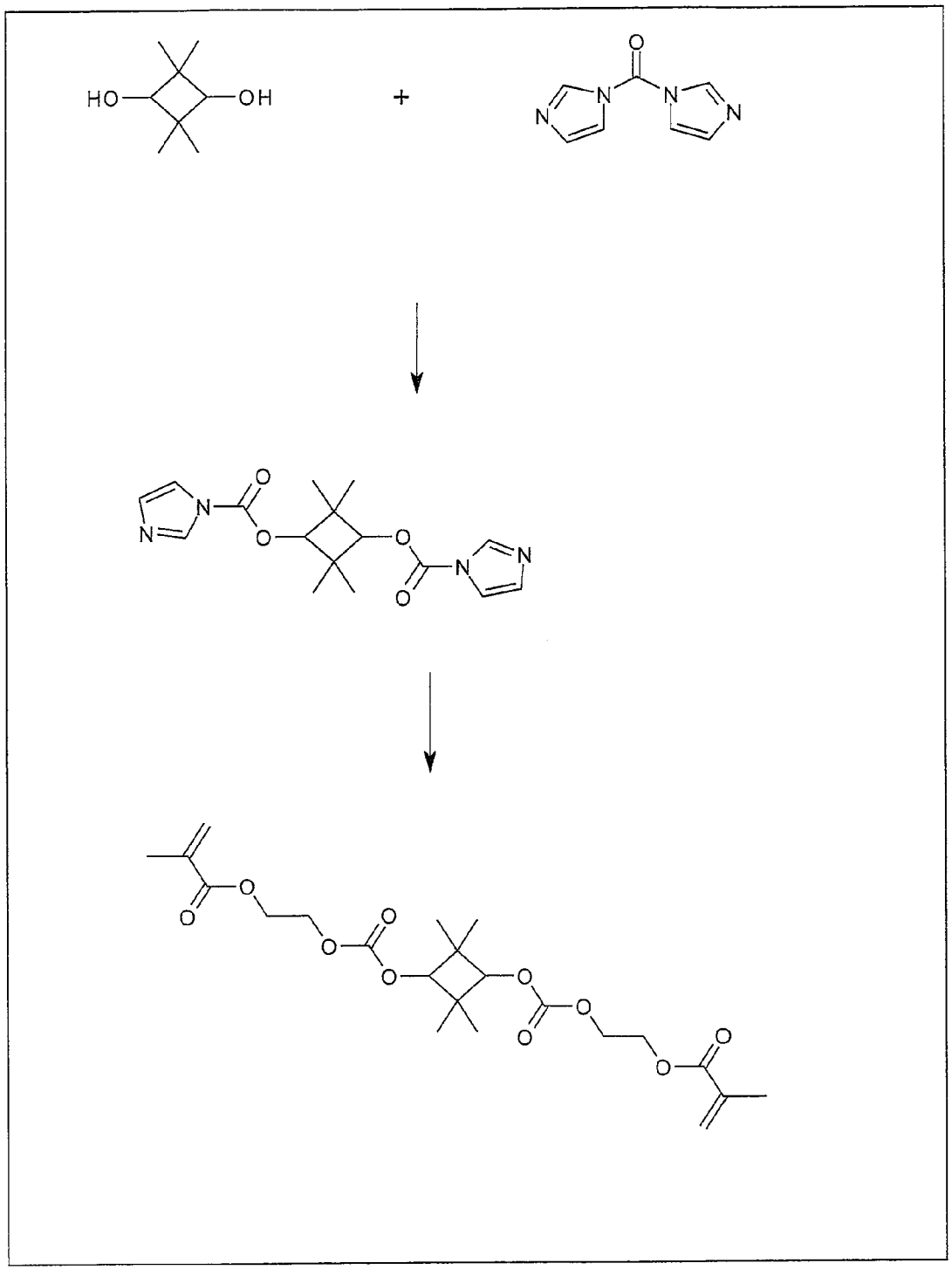
FIG. 4 shows a reaction pathway of creating a carbonate dimethacrylate trimer of a TMCD-based resin.

In FIG. 4, another reaction pathway towards carbonate type of polymerizable resin based on TMCD is further illustrated. This resulting carbonate resin is semi-crystalline with a melting point of about 68° C. This resin can be formulated with other resins and conventional initiators to make it polymerizable. Thus, clear, rigid cured resin can be resulted after it is formulated with CQ/EDAB and exposed to visible light.

The polymerizable TMCD-based composition according to the invention may includes a filler, stabilizer, polymerization initiator or cure package, or the like. The filler may be an inorganic filler and/or an organic filler. Preferred fillers for use in compositions in accordance with the invention include inorganic fillers, such as colloidal silica, alumina, zinc oxide, zirconia, magnesia, titania, and the like may also be used, or an organic fillers, such as polymer granulate or a combination of organic/or inorganic fillers. Total filler loading should vary from about 1 weight percent to about 95 weight percent, such as from about 5 weight percent to about 95 weight percent. In Table II and III, it is shown some examples of formulated TMCD-based resin systems and their corresponding composites with 40% of filler loading. Obviously extremely low curing stress can be resulted from the newly formulated BPA-free resin systems though they offer only slightly low shrinkage in comparison to a BPA-containing resin (TPH resin, a urethane-modified BisGMA derivative).

The dental composition described herein may include TMCD, a diluent, a filler and optional photoinitiator compounds. TMCD may be present in the dental composition in amounts for from about 5 weight percent to about 95 weight percent, such as from about 5 weight percent to about 70 weight percent or from about 5 weight percent to about 60 weight percent. A diluent may be present in the dental composition in amounts for from about 5 weight percent to about 50 weight percent, such as from about 5 weight percent to about 35 weight percent or from about 10 weight percent to about 30 weight percent. A filler may be present in the dental composition in amounts for from about 10 weight percent to about 90 weight percent, such as from about 20 weight percent to about 80 weight percent or from about 30 weight percent to about 70 weight percent. Photoinitiator compounds may be present in the dental composition in amounts of from about 0.01 weight percent to about 5 weight percent, such as from about 0.05 weight percent to about 1 weight percent or from about 0.1 weight percent to about 0.5 weight percent.

As explained herein the dental compositions disclosed herein may be a dental cement, a dental sealer, a dental restorative, or the like.

A exemplary cement in accordance with a preferred embodiment of the invention for dental and/or medical use includes a TMCD monomer or co-monomer having at least one polymerizable group in an amount of from about 10 to about 30 percent by weight, a polymerizable monomer as a diluent and a stabilizer in an amount of from about 15 to about 35 percent by weight, a filler in an amount of from about 50 to about 65 percent by weight, and the polymerization initiator component(s) in an amount of from about 0.05 to about 0.5 percent by weight.

A composite restorative composition in accordance with a preferred embodiment of the invention for dental and/or medical use includes a TMCD monomer or co-monomer having at least one polymerizable group in an amount of from about 5 to about 25 percent by weight, a polymerizable monomer as a diluent and a stabilizer in an amount of from about 5 to about 20 percent by weight, a filler in an amount of from about 50 to about 85 percent by weight, and the polymerization initiator component(s) in an amount of from about 0.05 to about 0.5 percent by weight.

A dental/medical sealer in accordance with a preferred embodiment of the invention for dental and/or medical use includes a TMCD monomer or co-monomer having at least one polymerizable group in an amount of from about 15 to about 55 percent by weight, a polymerizable monomer as a diluent and a stabilizer in an amount of from about 20 to about 40 percent by weight, a filler in an amount of from about 10 to about 50 percent by weight, and the polymerization initiator component(s) in an amount of from about 0.05 to about 0.5 percent by weight.

The dental compositions disclosed herein may be made by any suitable method. As an example, the dental compositions disclosed herein may be made by first forming the TMCD resin described herein. As described in detail in the examples below and the attached figures, this can be done by reacting a TMCD diol with an isocyante or a carboxylic monomer. The formed TMCD resin is then combined with optional diluents, filler, photoinitiator compounds, and any other components described herein in order to create the formulated TMCD resin. These components may be combined or mixed by any suitable method. This formulated TMCD resin is then combined with any suitable surface-modified glass filler in order to generate the dental composition described herein. The formulated TMCD resin and suitable glass filler may be combined or mixed by any suitable method in order to form the dental composition described herein. As particulate filler, it includes colloidal silica, alumina, zinc oxide, zirconia, magnesia, titania, and the like may also be used.

The resulting dental composition disclosed herein exhibits improved characteristic, such as improved compressive yield strength and improved compressive modulus. The dental composition may exhibit a compressive yield strength of from about 80 MPa to about 300 MPa, such as from about 90 MPa to about 250 MPa or such as from about 100 MPa to about 200 MPa. The dental composition may exhibit a compressive modulus of from about 2000 MPa to about 5000 MPa, such as from about 2250 MPa to about 4500 MPa or from about 2500 MPa to about 4000 MPa.

Experiments and Test Methods:

Resin Synthesis: A solvent-free process is employed for urethane resin synthesis and solvent has to be used in carbonate-type of resin process.

TMCD Resin 1: Urethane dimethacrylate oligomer was prepared by a one-step condensation reaction from a preformed monohydroxy-monomethacrylate (ICEM) from 2,4,4-(2,2,4)-trimethyl-hexanediisocyanate (TMDI) and 2-hydroxyethoxylmethacrylate (HEMA), and TMCD (about 0.02 mol) in the presence of dibutyltin dilaurate under a dry air atmosphere at a temperature from about 30° C. to about 35° C. for about 14 hours. To the reaction system, 2,6-di(tert-butyl)-4-methylphenol, BHT was also added as an inhibitor. See FIG. 2.

TMCD Resin 2: Urethane dimethacrylate trimer was prepared by a one-step condensation reaction from TMCD and 2-isocyanateethyl methacrylate (IEM). The first reaction was carried out in the presence of dibutyltin dilaurate under a dry air atmosphere at a temperature from about 30° C. to about 35° C. for about 4 hours. To the reaction system, BHT was also added as an inhibitor and TEGDMA can also be used as an inert diluent for this reaction. Semicrystallime resin could be developed after aging at room temperature. See FIG. 3.

TMCD Resin 3: Carbonate dimethacrylate trimer was prepared by a one-step condensation reaction from TMCD and mono-2-(methacryl-oxy)ethyl-succinate (HEMASA) in solvent (methylene dichloride) in the presence of N,N'-dicyclohexylcarbodiimide, DCC under a dry air atmosphere at room temperature, that is, a temperature of from about 20° C. to about 26° C. To the reaction system, BHT was also added as inhibitor. Semi-crystalline resin could be slowly developed at RT aging after the solvent was removed from the resin system. See FIG. 4.

TMCD Resin 4: Urethane dimethacrylate oligomers were prepared by a two-step condensation reaction from TMCD and slight excess of isophorone diisocyanate, IPDI, followed by a reaction between the NCO-terminated prepolymer and 2-hydroxyethyl methacrylate. The first reaction was carried out in the presence of dibutyltin dilaurate under a dry air atmosphere at a temperature from about 30° C. to about 35° C. for about 4 hours. To the resulting prepolymer, BHT was added as an inhibitor. See FIG. 5.

TMCD Resin 5 and 6: Triethyleneglycol dimethacylate (TEGDMA) was used as inert diluent in this process for the urethane dimethacrylate oligomers, were prepared by a two-step condensation reaction from TMCD and a slight excess of TMDI or IPDI in the presence of dibutyltin dilaurate under a dry nitrogen atmosphere at a temperature from about 30° C. to about 35° C. for about 4 hours to form NCO-terminated prepolymers, followed by end-capping reaction with 2-hydroxyethyl methacrylate. BHT was added as an inhibitor. See FIGS. 6 and 5, respectively.

TMCD Resin 7: TEGDMA was also used as inert diluent in this process for this urethane dimethacrylate oligomers were prepared by a two-step condensation reaction from TMCD and a slight excess of TMDI or IPDI in the presence of T-9 catalyst under a dry air atmosphere at a temperature from about 30° C. to about 35° C. for about 4 hours to form NCO-terminated prepolymers, followed by end-capping reaction with 2-hydroxyethyl methacrylate. BHT was added as an inhibitor. Since the reaction was so slow, additional dibutyltin dilaurate had to be added to ensure a complete reaction of TMCD. See FIG. 6.

Formulated Resin 1 through 7 showed further formulated resin compositions, which are comprised of TMCD-based polymerizable resins (TMCD Resin 1-7) as described previously, and other conventional (meth)acrylate resins and a variety of photoinitaitors (CQ, 2,4,6-trimethylbenzoyldiphenylphosphine oxide, LTPO etc). A comparable example 1 is also included here with exclusion of any TMCD-based resins mentioned herein.

Formulated Pastes 1 through 7 showed those formulated composite compositions, which are comprised of a variety of formulated TMCD-based polymerizable resins as previously described, and about 40% wt/wt of glass filler mixtures. A comparable example 2 is also included here with exclusion of any TMCD-based resins mentioned herein.

Photo DSC: DSC 2529 with photocaltometer (TA Instrument) was used to evaluate the photolysis and photopolymerization for the neat resin and/or any formulated resin system. The test was performed under both air and nitrogen. The light outputs and light spectrum can be tuned by using build-in filter, or additional UV filter or intensity-reducing filter.

Flexural strength and modulus ere tested according to ISO 4049, 2×2×25 mm specimens were cured by three overlapped spot curing with Spectrum 800 with 13=light guide at 800 mw/cm², 20" for each spot on one side only. The cured specimens (6-10) were placed in deionized water and stored at about 37° C. for about 24 hours, then were sanded prior to the test at room temperature, about 25° C.

Compressive strength and modulus were tested according to ISO 9917, which is actually for water-based cements since ISO 4049 does not specify for compressive strength. φ4×6 mm glass slave was used as a mold for specimen preparation (6). It was cured by Spectrum 800 at about 800 mw/cm² from both top and bottom, at about 20" each. The cured specimens (6-10) were placed in deionized water and stored at about 37° C. for about 24 hours, and then were sanded prior to the test at room temperature.

Polymerization Shrinkage was calculated from the density change before and after curing, which were measured by helium pycnometer (Microineritics, AccuPyc II 1340) at about 25° C. New in-house shrinkage test protocol was followed in this test: 3 pieces of round disc samples from a φ10×2=Teflon mold. It was pressed between Mylar films and cured by Spectrum 800 at about 800 mw/cm² for about 20 seconds from top and bottom sides, respectively. The cured specimen was stored at room temperature for 2-3 hrs or for 24 hrs prior to the density measurement.

Shrinkage Stress was measured by using NIST/ADA's tensometer. Specimen with 2.25 mm thickness (c-factor as 1.33) is cured for 60 seconds by DENTSPLY/Cauk's QHL light at 550 mw/cm2. The total stress at the $60^{th}$ minute is taken to rank different materials.

UV-Vis Spectroscopy was measured by using Thermo Scientific's Evolution 160 UV-Vis spectrometer. Thin film of 25-200 microns was casted directly onto a fussed silica plate with a specially-fabricated stage.

Photo-Rheology: Light curable resins or composites were analyzed using two types of curing accessories (EXFO Omnicure 52000 with visible light filter and UV LED) in TA Instruments' AR-G2 rheometer at room temperature. Sample gap is 500 microns, Light intensity of 150 mw/cm² (visible light) or 120 mW/cm² (UV LED light) for 1 min or 5 min curing, respectively.

TABLE Ia

Compositions for Three Types of TMCD-based Polymerizable Resins

|  | TMCD Resin 1 | TMCD Resin 2 | TMCD Resin 3 |
|---|---|---|---|
| Resin Type | Urethane Oligomer | Urethane Trimer | Carbonate Trimer |
| TMCD-based Resin, | 95 | 78 | 100 |
| TEGDMA, | 5 | 10 | 0 |
| HEMA, (wt/wt, %) | 0 | 12 | 0 |
| Resin Form | Liquid | Semicrystalline | Semicrystaline |
| $T_m$(° C.) | None | 110 | 68 |

TABLE Ib

Compositions for Various Urethane Type of MCD-based Polymerizable Resins

|  | TMCD Resin 4 | TMCD Resin 5 | TMCD Resin 6 | TMCD Resin 7 |
|---|---|---|---|---|
| Resin Composition | TMCD/IPDI/HEMA/TEGDMA | TEGDMA/TMCD/TMDI/HEMA | TEGDMA/TMCD/IPDI/HEMA | TEGDMA/TMCD/TMDI/HEMA |
| TMCD-based Resin, | 77 | 72 | 67 | 72 |
| TEGDMA, | 17 | 15 | 23 | 15 |
| HEMA, | 2 | 4 | 2 | 4 |
| UDMA, (wt/wt, %) | 4 | 9 | 8 | 9 |
| Resin Form | Liquid | Liquid | Liquid | Liquid |
| Viscosity @ 20° C. Pa·s | 14350 | 75 | 1010 | 90 |
| RI @ 25° C. | N/A | 1.48426 ± 0.00045 | 1.49148 ± 0.00058 | N/A |

TABLE II

Physical Property for Formulated Urethane Type of TMCD-based Resins

|  | Formulated TMCD Resin 4 | Formulated TMCD Resin 5 | Formulated TMCD Resin 6 | Formulated TMCD Resin 7 |
|---|---|---|---|---|
|  | 100% TMCD Resin 5 | 80% TMCD Resin 6 13% TEGDMA 7% UDMA | 81.8% TMCD Resin 5 18.2% TEGDMA | 80% TMCD Resin 7 20% TMPTMA |
|  | 0.165% CQ 0.30% EDAB 0.030% BHT | 0.165% CQ 0.30% EDAB 0.030% BHT | 0.165% CQ 0.30% EDAB 0.030% BHT | 0.165% CQ 0.30% EDAB 0.030% BHT |
| Viscosity@20° C., Pa·s | 60 | 30 | 5 | 15 |
| Shrinkage @ 24 hrs, % | 5.94 | 6.14 | 7.79 | 7.09 |
| Stress @ 60 min, MPa | 1.30 | 1.64 | 1.89 | 1.63 |
| Compressive Yield St.(MPa) | 115 ± 1 | 135 ± 4 | 108 ± 1 | 114 ± 1 |
| Compressive Modulus(MPa) | 2630 ± 270 | 2700 ± 210 | 2510 ± 100 | 2600 ± 160 |
| Flexural St.(MPa) | 82 ± 2 | 64 ± 1 | 84 ± 2 | 69 ± 2 |
| Flexural Modulus(MPa | 1780 ± 70 | 1700 ± 130 | 1830 ± 110 | 1380 ± 130 |

TABLE IIIa

Property for Various Formulated Composites containing TMCD-based Resins

| | Formulated Paste 1 | Formulated Paste 2 |
|---|---|---|
| Resins (wt/wt, %) | TMCD Resin 2<br>60 | TMCD Resin 3<br>60 |
| Fillers (wt/wt, %) | 40 | 40 |
| Viscosity@35° C. Pa·s | 30 | 20 |
| Shrinkage @ 72 hrs % | 5.61 | NA |
| Stress @ 60 min MPa | 0.93 | 1.00 |
| Compressive Yield St.(MPa) | 121 ± 2 | 102 ± 2 |
| Compressive Modulus(MPa) | 3210 ± 400 | 3100 ± 250 |
| Flexural St.(MPa) | 78 ± 5 | 70 ± 5 |
| Flexural Modulus(MPa) | 2620 ± 140 | 2580 ± 200 |

TABLE IIIb

Property for Formulated Composites Containing TMCD-based Resins

| | Formulated Paste 4 | Formulated Paste 5 | Formulated Paste 6 | Formulated Paste 7 |
|---|---|---|---|---|
| Resins (wt/wt, %) | Formulated TMCD Resin 4<br>60 | Formulated TMCD Resin 5<br>60 | Formulated TMCD Resin 6<br>60 | Formulated TMCD Resin 7<br>60 |
| Fillers (wt/wt, %) | 40 | 40 | 40 | 40 |
| Viscosity @35° C. Pa·s | 22 | 10 | 3 | 8 |
| Shrinkage @ 24 hrs % | 4.36 | 5.19 | 6.39 | 5.71 |
| Stress @ 60 min MPa | 0.91 | 0.76 | 1.22 | 1.28 |
| Compressive Yield St.(MPa) | 116 ± 3 | 115 ± 5 | 109 ± 3 | 118 ± 3 |
| Compressive Modulus(MPa) | 3220 ± 440 | 3070 ± 310 | 3660 ± 190 | 2260 ± 350 |
| Flexural St.(MPa) | 91 ± 2 | 64 ± 1 | 92 ± 2 | 84 ± 1 |
| Flexural Modulus(MPa) | 2710 ± 240 | 1700 ± 130 | 2650 ± 170 | 2480 ± 80 |

TABLE IVa

Physical Property for Control Urethane Resins

| | Control Resin 1 | Control Resin 4 |
|---|---|---|
| Composition | 100% UDMA<br>0.165% CQ<br>0.30% EDAB<br>0.030% BHT | 75% BisGMA<br>25% TEGDMA<br>0.165% CQ<br>0.30% EDAB<br>0.030% BHT |
| Viscosity@20° C. Pa·s | 25 | 5 |
| Shrinkage @ 24 hrs % | 6.86 | 7.42 |
| Stress @ 60 min MPa | 0.99 | 2.98 |
| Compressive Yield St.(MPa) | 97 ± 3 | 122 ± 2 |
| Compressive Modulus(MPa) | 2200 ± 150 | 2880 ± 140 |
| Flexural St.(MPa) | 62 ± 2 | 108 ± 7 |
| Flexural Modulus(MPa) | 1200 ± 70 | 2370 ± 60 |

TABLE IVb

Property for Composites based on Control Urethane Resins

| | Control Paste 1 | Control Paste 2 | Control Paste 3 | Control Paste 4 |
|---|---|---|---|---|
| Control Resins (wt/wt, %) | UDMA<br>60 | TPH Resin<br>60 | SDR/TEGDMA<br>60 | BisGMA/TEGDMA<br>60 |
| Fillers (wt/wt, %) | 40 | 40 | 40 | 40 |
| Viscosity@35° C. Pa·s | 8 | 8 | 12 | 3 |
| Shrinkage @ 24 hrs % | 5.22 | 6.05 | 4.95 | 5.51 |

TABLE IVb-continued

Property for Composites based on Control Urethane Resins

|  | Control Paste 1 | Control Paste 2 | Control Paste 3 | Control Paste 4 |
|---|---|---|---|---|
| Stress @ 60 min MPa | 1.17 | 3.88 | 1.24 | 2.57 |
| Compressive Yield St.(MPa) | 102 ± 3 | 130 ± 3 | 121 ± 5 | 133 ± 3 |
| Compressive Modulus(MPa) | 2530 ± 170 | 3160 ± 220 | 3370 ± 170 | 3940 ± 170 |
| Flexural St.(MPa) | 79 ± 4 | 101 ± 9 | 97 ± 3 | 108 ± 8 |
| Flexural Modulus(MPa | 2000 ± 80 | 3520 ± 110 | 2750 ± 190 | 3920 ± 220 |

Although there are many commercially-available resins that are BPA-free, such as TEGDMA, UDMA and other types of (meth)acrylic resins, there is still strong desire for new BPA-free resin as anchor resin to provide adequate mechanical performance. Described herein are reaction processes to incorporate TMCD into a radically polymerizable resin as part of a BPA-free resin platform for dental applications.

Chemically, TMCD is a diol molecule and it should be readily reacted with other condensation monomers to build up linkages like ester, carbonate, urethane, etc. (see FIGS. 1a and 1b) and to form polymerizable resins, accordingly. For example, If TMCD reacts with an isocyanate, it would yield a urethane type of resin; if TMCD reacts with a carboxylic monomer, then it would yield an ester type of resin. Obviously, the physical and mechanical properties of the resulting TMCD-based resins would vary depending upon the resin's linkages, detailed molecular structures and the pathways to make such resins.

Since TMCD is a highly symmetrical molecule, there are certain limitations in choosing its co-reactants for such reactions in order to yield a liquid resin, not crystal or semicrystalline ones, even though its cis/trans isomers are used. Therefore, our initial pathway to make TMCD-based resin is urethane type. Thus TMCD reacted with a monoisocyanate derivative (1-methacryloxylethylurethane-2,4,4(2,2,4)-trimethyl-6-hexaneisocuynate, ICEM) to form new TMCD-based urethane resins. As showed in FIG. 2, for example, a urethane type resin containing TMCD was achieved by reacting TMCD and ICEM. ICEM is a resin mixture comprising preformed monoisocyanate methacrylate and dimethecrylate. Accordingly, the resulting TMCD-based urethane resin containing other dimethacrylates such as UDMA and TEGDMA and slight excess of HEMA. In addition, it was found that the reactivity of such secondary diol in TMCD was dramatically reduced towards ICEM, which was attributed to the steric hindrances from both TMCD and the isocyanate. Therefore, small amount of TMCD might remain as unreacted or partially reacted. It is a high viscose but colorless liquid resin (TMCD Resin 1). Additional diluent was used to formulate a workable resin as showed in Table IIa (Formulated TMCD Resin 3). The evaluation of this batch of BPA-free resin showed a shrinkage of 6.8% and low stress of 1.06 MPa.

As illustrated in FIG. 1, TMCD may be incorporated into polymerizable resin via a variety of approaches. For example, TMCD-based polymerizable resin may be achieved by using diisocyanate, thus yielding a urethane type of oligomer resin in liquid form (see FIG. 2). However, it was found that some of unreacted and/or partially reacted TMCD remained in the resin mixture due to low reactivity nature of TMCD towards a sterically hindered isocyanate. Therefore, a highly reactive monoisocyanate (IEM) was used to ensure TMCD fully reacted. As showed in FIG. 3, the reaction of TMCD and IEM should yield a urethane trimer (TMCD Resin 2). Unfortunately, such a well-defined trimer is in a semicrystalline form due to the chain regularity and strong H-bonding.

In addition, carbonate type of TMCD-based resin as showed in FIG. 4 was also explored in order to reduce viscosity and minimize tackiness that may be caused by strong H-bonding in resin matrix. Unlike urethane type of resin, there is no H-bonding within this carbonate type of trimer resin (TMCD Resin 3). Although no diluent was needed during the reaction, the resulting carbonate resin was found to recrystallize quickly.

Due to the crystallinity of these two trimer resins, only 20% of the TMCD resin was incorporated into the formulated resins for evaluation as showed in Table II. Such a resin mixture was in liquid form. As expected, low stress resulted from the formulated resin systems. More importantly, they also offered moderate mechanical property, for example, a flexural strength of 75 MP and compressive yield strength of 156 MPa for Formulated TMCD Resin 1 in Table IIa.

Figure 5:
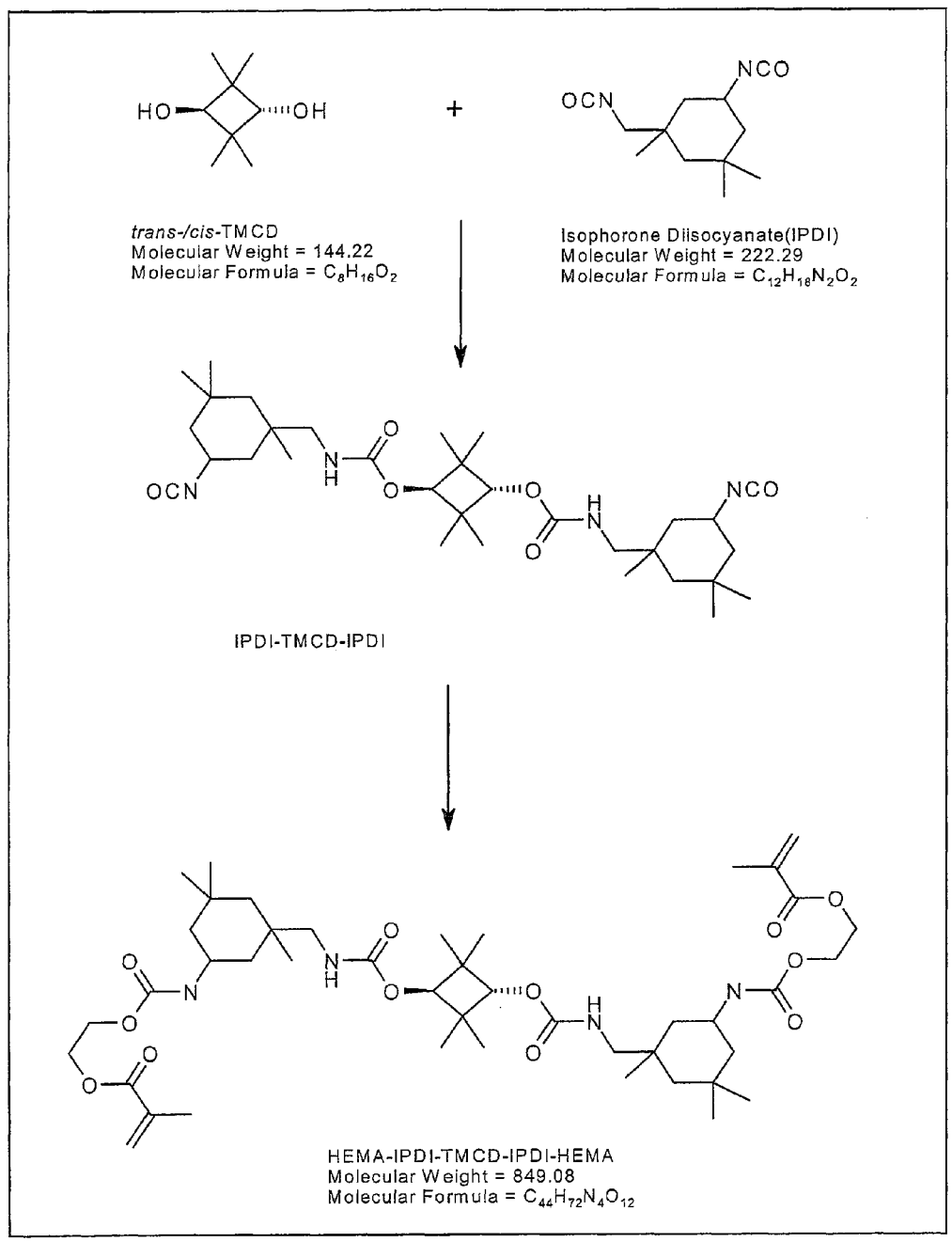
FIG. 5 shows a two-step condensation reaction pathway of a urethane dimethacrylate oligomer of a TMCD-based resin.

Because the TMCD trimeric resins with well-defined structures yielded the crystalline resins and the TMCD resin was an amorphous liquid, TMCD was reacted with an asymmetric diisocyanate monomer (isophorone diisocyanate, IPDI, as shown in FIG. 5) with the belief that it might disrupt the chain regularity and yield an amorphous resin with improved TMCD conversion because of the initial low viscosity of the IPDI/TMCD system. A stepwise addition of TMCD ensured a smooth early reaction, but the bulk viscosity increased as the reaction proceeded. In order to ensure a complete conversion of TMCD, solvent had to be added to the reaction system prior to HEMA being introduced. Then diluent (TEGDMA) was loaded into the system prior to stripping off the solvent. The viscosity of such TMCD resin was still quite high, about 14,500 Pa·s at about 20° C., for the final resin mixture though there was about 17% of TEGDMA (see Table I). In order to formulate a workable resin from such high viscose resin, more diluent has to be incorporated. It yielded a low stress though its shrinkage was about 5.6%.

Although the chemical reaction in TMCD/IPDI/HEMA system proceeded as expected in term of improving TMCD conversion, its high viscosity for TMCD Resin 4 was unexpected. Such a high viscosity limited the application of the resin. In order to formulate a workable resin from such high viscose resin, more diluent has to be incorporated.

Figure 6:
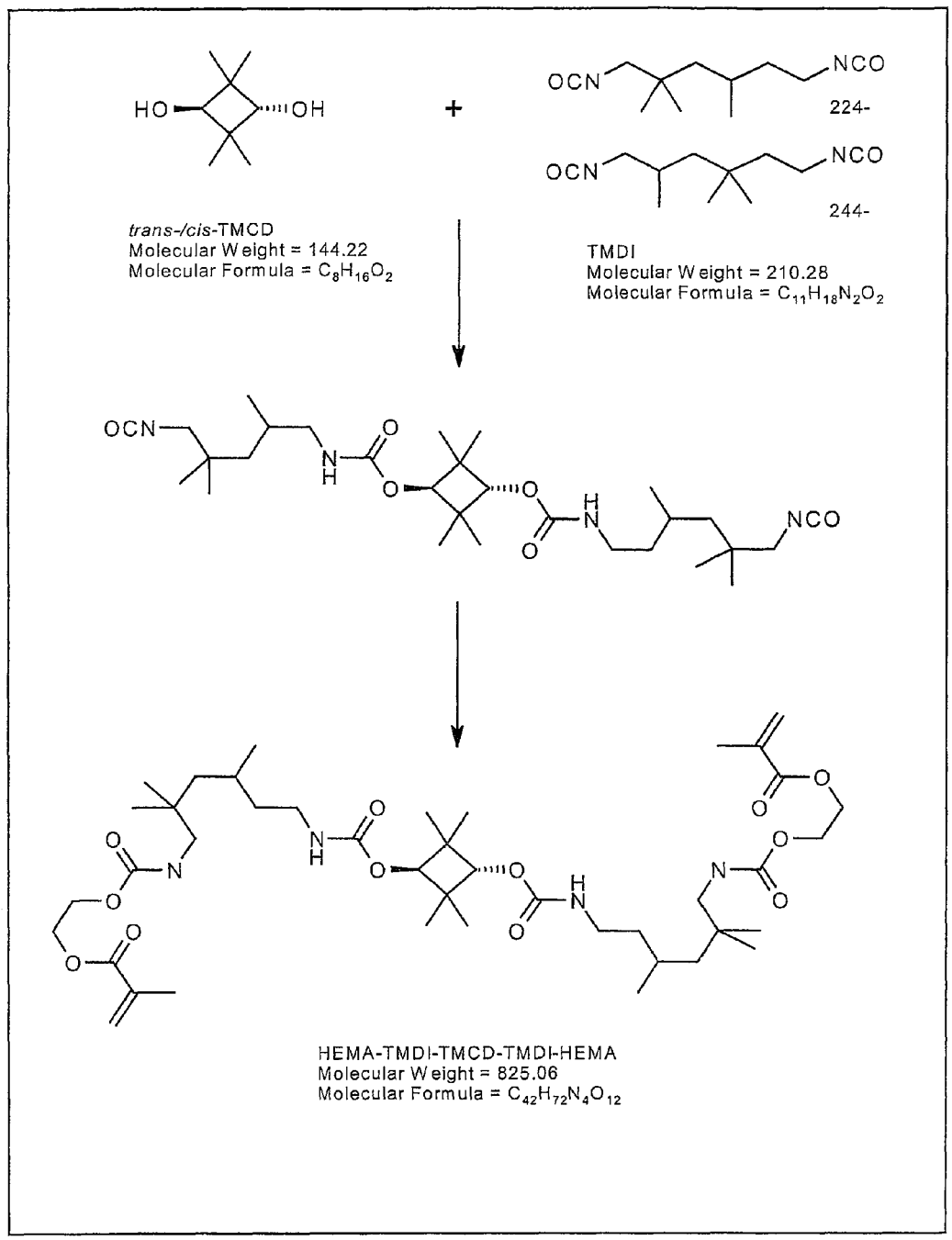
FIG. 6 shows another two-step condensation reaction pathway of a urethane dimethacrylate oligomer of a TMCD-based resin.

Another diisocyanate, TMDI, was then used in synthesizing TMCD-based urethane resin. As illustrated in FIG. 6, TMDI is an asymmetrical diisocyanate, which was expected to offer an effective disruption of the crystallinity of resulting urethane resins and also to effectively control the viscosity of the resulting urethane resins. In addition, TEGDMA was also incorporated into the reaction system as solvent in the early reaction stage to ease the reaction of crystalline TMCD with TMDI (TMCD Resin 5). Surprisingly, the viscosity of such a resin was well controlled. As showed in Table I, a low viscosity of about 75 Pa·s at about 20° C. with more than 70% wt/wt of TMCD resin fraction was achieved. Its refractive index was about 1.4843 as measured at about 25° C.

However, when a similar reaction process was applied to IPDI, a high viscosity resin was achieved (TMCD Resin 6) and slight gelation was also noted during the second stage reaction of the resin system.

Both TMCD Resin 5 and TMCD Resin 6 were evaluated as resins and filled composites, which are shown in Table IIb and Table IIIb, respectively. No additional diluents were used in formulation of TMCD Resin 5, in comparison to the 20 weight % diluents that were used in formulating TMCD Resin 6. Both resins yielded relatively low polymerization stress of from about 1.30 MPa to about 1.65 MPa, although both resins showed a polymerization shrinkage of about 6.0%. As shown in Tables II and III, moderate mechanical strength and modulus resulted from the cured resin specimen, which indicated that proper conversions were achieved. For the filled composites, slightly lower polymerization shrinkage resulted but much lower polymerization stress was developed. Again, moderate mechanical property was demonstrated by Formulated TMCD Paste 4, which was formulated from the new resin TMCD Resin 5.

In addition, four more control resins (UMDA, TPH Resin, SDR Resin, and BisGMA/TEGDMA, see Table IVa) and their composites with 40% wt/wt of BAFG filler mix (Table IVb) were evaluated as a comparison to several formulated TMCD-based urethane resins (Tables IIa and IIb) and their composites with 40% wt/wt of BAFG filler mix (Tables II and IIIb).

With similar viscosity, TPH resin (XJ7-161-2) showed slightly higher polymerization shrinkage (7.35%) than other three resins (6.73-6.86%), but it also generated a significantly high polymerization stress than others, 4.38 MPa vs. 0.99-2.98 MPa. The resin with the lowest MW (UDMA) offered the least polymerization stress but its overall mechanical property is lower than TPH resin.

The Formulated TMCD Resins and composites from the TMCD-based resins (TMCD/IPDI/HEMA/TEGDMA (TMCD Resin 4 and TMCD Resin 6) and TMCD/TMDI/HEMA/TEGDMA (TMCD Resin 5 and TMCD Resin 7) exhibit low shrinkage of from about 5.6% to about 7.1% and polymerization stress of from about 1.3 MPa to about 1.6 MPa (Tables II and IIIb).

It should be evident that the dental composition disclosed herein carries out one or more of the objects set forth above and otherwise constitutes an advantageous contribution to the art. As will be apparent to persons skilled in the art, modifications can be made to the embodiments disclosed herein without departing from the spirit of the disclosure.

What is claimed:

1. A dental composition comprising a liquid dental resin and a dental filler, wherein the dental resin is derived from 2,2,4,4-tetramethyl-1,3-cyclobutanediol, a diisocynate, and a monohydroxylmethacrylate.

2. The dental composition according to claim 1, wherein the dental composition upon curing exhibits a compressive yield strength of from about 80 MPa to about 300 MPa.

3. The dental composition according to claim 2, wherein the compressive yield strength is from about 90 MPa to about 250 MPa.

4. The dental composition according to claim 3, wherein the compressive yield strength is from about 100 MPa to about 200 MPa.

5. The dental composition according to claim 1, wherein the dental composition upon curing exhibits a compressive modulus of from about 2000 MPa to about 5000 MPa.

6. The dental composition according to claim 5, wherein the compressive modulus is from about 2250 MPa to about 4500 MPa.

7. The dental composition according to claim 6, wherein the compressive modulus is from about 2500 MPa to about 4000 MPa.

8. The dental composition according to claim 1, wherein the dental filler is selected from the group consisting of colloidal silica, alumina, zinc oxide, zirconia, magnesia, and titania.

9. The dental composition according to claim 1, wherein the dental filler is present in the dental composition in an amount from about 5 weight percent to about 95 weight percent.

10. The dental composition according to claim 1, wherein the dental resin is present in an amount from about 5 weight percent to about 95 weight percent and the dental filler is present in an amount from about 5 weight percent to about 95 weight percent.

11. The dental composition according to claim 1, wherein the dental composition is a dental cement, a dental sealer or a dental restorative.

12. A method of producing a dental composition, comprising:
reacting 2,2,4,4-tetramethyl-1,3-cyclobutanediol (TMCD) with diisocyanate and monohydroxyl(meth)acrylate to create a liquid TMCD-based resin, and
mixing the TMCD-based resin with a dental filler to form the dental composition.

13. The method according to claim 12, wherein the dental composition is a dental cement, a dental sealer or a dental restorative.

14. The method according to claim 12, wherein the TMCD-based resin is present in an amount from about 5 weight percent to about 95 weight percent and the dental filler is present in an amount from about 5 weight percent to about 95 weight percent.

15. The method according to claim 12, wherein the dental filler is selected from the group consisting of $La_2O_3$, $ZrO_2$, $BiPO_4$, $CaWO_4$, $BaWO_4$, $SrF_2$ and $Bi_2O_3$.

16. The method according to claim 12, further comprising curing the dental composition, and wherein the dental composition upon curing exhibits a compressive yield strength of from about 100 MPa to about 300 MPa.

17. The method according to claim 12, further comprising curing the dental composition, and wherein the dental composition upon curing exhibits a compressive modulus of from about 2000 MPa to about 5000 MPa.

* * * * *